(12) United States Patent
Towler et al.

(10) Patent No.: US 8,624,074 B2
(45) Date of Patent: Jan. 7, 2014

(54) REACTOR FLOWSCHEME FOR DEHYDROGENATION OF PROPANE TO PROPYLENE

(75) Inventors: Gavin P. Towler, Inverness, IL (US); Cynthia K. Zimmerman, Palatine, IL (US)

(73) Assignee: UOP LLC, Des Plaines, IL (US)

( * ) Notice: Subject to any disclaimer, the term of this patent is extended or adjusted under 35 U.S.C. 154(b) by 405 days.

(21) Appl. No.: 12/728,543

(22) Filed: Mar. 22, 2010

(65) Prior Publication Data
US 2011/0230698 A1   Sep. 22, 2011

(51) Int. Cl.
*C07C 5/333* (2006.01)

(52) U.S. Cl.
USPC ........... 585/659; 585/654; 585/660; 585/661; 585/662; 585/663

(58) Field of Classification Search
USPC ................ 585/654, 659, 660, 661, 662, 663
See application file for complete search history.

(56) References Cited

U.S. PATENT DOCUMENTS

| | | | |
|---|---|---|---|
| 4,851,374 A * | 7/1989 | Yan et al. | 502/42 |
| 5,254,788 A | 10/1993 | Gartside | |
| 5,633,421 A * | 5/1997 | Iezzi et al. | 585/660 |
| 6,045,688 A | 4/2000 | Ruottu | |
| 6,242,660 B1 * | 6/2001 | Buonomo et al. | 585/445 |
| 6,362,385 B1 * | 3/2002 | Iezzi et al. | 585/661 |
| 6,576,804 B1 * | 6/2003 | Heineke et al. | 585/661 |
| 7,235,706 B2 | 6/2007 | Iezzi et al. | |
| 2002/0183573 A1 * | 12/2002 | Cocco et al. | 585/444 |
| 2008/0097134 A1 | 4/2008 | Fridman et al. | |
| 2008/0161624 A1 * | 7/2008 | Glover et al. | 585/634 |
| 2009/0012341 A1 | 1/2009 | Brophy et al. | |
| 2009/0240094 A1 | 9/2009 | Crone et al. | |

FOREIGN PATENT DOCUMENTS

| CN | 1912065 A1 | 2/2007 |
|---|---|---|
| RU | 2214383 C1 | 10/2003 |

OTHER PUBLICATIONS

Werther, "Fluidized-Bed Reactors" in Ullmann's Encyclopedia of Industrial Chemistry, 2007, Wiley-VCH, available on-line Apr. 15, 2007.*
Bhasin et al., "Dehydrogenation and oxydehydrogenation of paraffins to olefins," Applied Catalysis A: General 221 (2001) p. 397-419.
Gascon et al., "A two-zone fluidized bed reactor for catalytic propane dehydrogenation," Chemical Engineering Journal 106 (2005) p. 91-96.
Kotelnikov et al., "Application of FBD processes for C3-C4 olefins production from light paraffins," Studies in Surface Science and Catalysis, p. 67-72, vol. 147, 2004 Elsevier.

(Continued)

*Primary Examiner* — In Suk Bullock
*Assistant Examiner* — Bradley Etherton
(74) *Attorney, Agent, or Firm* — Arthur E Gooding

(57) ABSTRACT

A process for the dehydrogenation of paraffins is presented. The process utilizes a rapid recycling of dehydrogenation catalyst between the dehydrogenation reactor and the catalyst regeneration unit. The process comprises preheating a combined hydrogen and paraffin hydrocarbon feedstream and passing the combined stream to a dehydrogenation reactor. The hydrocarbon feedstream and the catalyst pass through the reactor at a rate to limit the average residence time of the catalyst in the reactor. The catalyst is cycled to a regeneration unit, and passed through the regeneration unit to limit the average residence time of the catalyst in the regeneration unit.

18 Claims, 1 Drawing Sheet

(56) References Cited

OTHER PUBLICATIONS

Lobera et al., "Propane Dehydrogenation over Pt-Sn-K/y-Al2O3 Catalyst in a Two-Zone Fluidized Bed Reactor," Ind. Eng. Chem. Res. 2008, 47, p. 9314-9320.

Van Sint Annaland et al., "A novel reverse flow reactor coupling endothermic and exothermic reactions: an experimental study," Chem. Eng. Science 57 (2002) p. 4967-4985.

European Search Report dated Jul. 30, 2013, for European patent application No. 11759873.0-1451/2550245 PCT/US2011026171; applicant reference No. H0020809.

* cited by examiner

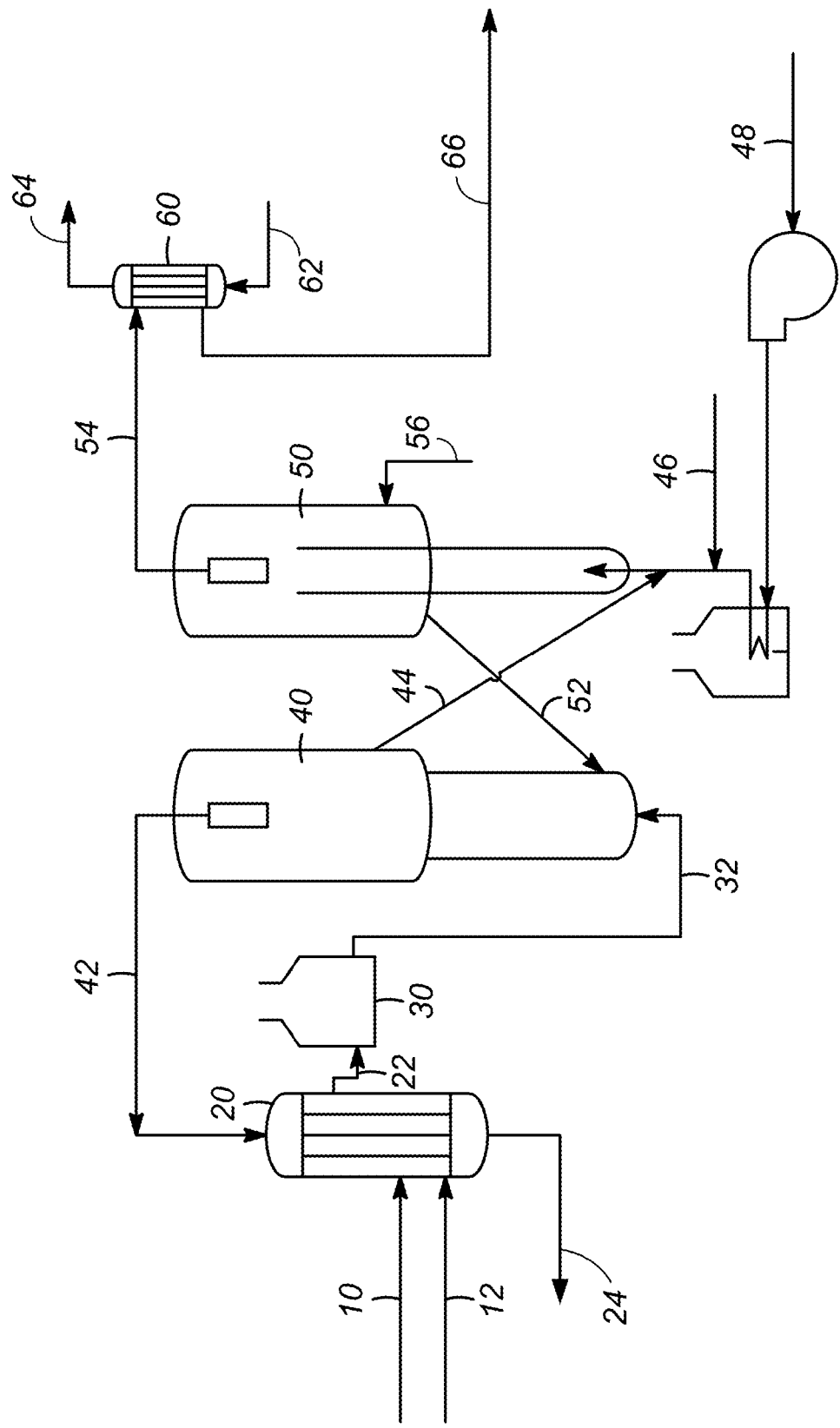

REACTOR FLOWSCHEME FOR DEHYDROGENATION OF PROPANE TO PROPYLENE

FIELD OF THE INVENTION

The present invention relates to the production of light olefins from paraffins. Specifically, the invention is directed at propane dehydrogenation in the production of propylene.

BACKGROUND OF THE INVENTION

Continuous catalyst conversion processes in the petrochemical industry. The fluidized catalyst cracking of hydrocarbons is an important process for the production of lighter hydrocarbon components, and it is an important process for the production of ethylene and propylene. The fluidized catalytic cracking process continuously circulates a fluidized catalyst between a reactor and a regenerator.

Another route for the production of propylene can be obtained by the dehydrogenation of propane through catalytic dehydrogenation. The dehydrogenation catalysts generally comprise noble metal catalysts on acidic supports, such as alumina, or silica alumina, or zeolitic materials. However, the reaction is strongly endothermic, and requires a high temperature for the reaction to proceed at a satisfactory rate. At the same time, the reactions need to be controlled to limit the degradation of the propane to form methane and ethylene, and where the ethylene can be hydrogenated by the hydrogen released through the dehydrogenation of the propane. The process also leads to coking of the catalyst, and deactivates the catalyst. The catalyst therefore needs to be regenerated on a regular basis after relatively short periods of operation, or residence, in the dehydrogenation reactor.

SUMMARY OF THE INVENTION

The present invention is a process for the dehydrogenation of paraffins. In particular, the process is for the dehydrogenation of propane for the production of propylene. The process comprises passing a preheated propane feedstream to a dehydrogenation reactor. The reactor is operated at conditions to mix and contact the propane with a fluidized catalyst to generate a product stream comprising propylene. The operation of the reactor is designed to continuously supply catalyst and remove catalyst from the dehydrogenation reactor at a rate to provide a residence time of the catalyst in the reactor between 15 and 45 minutes. The reactor is a fast fluidizing reactor to provide well mixed reactants and feedstream and to provide a uniform temperature over the reactor. The effluent stream from the reactor is separated into a spent catalyst stream and a product stream comprising propylene. The spent catalyst is passed to a catalyst regeneration unit, thereby generating a regenerated catalyst stream. The catalyst is processed in the regeneration unit under conditions to limit the average residence time in the regeneration unit to 30 minutes or less. The regenerated catalyst is passed to the dehydrogenation reactor.

The high cycling rate of catalyst through the reactor and regenerator allow for increasing the overall flow through of reactants, and increases the productivity of a dehydrogenation reactor.

Additional objects, embodiments and details of this invention can be obtained from the following drawings and detailed description of the invention.

BRIEF DESCRIPTION OF THE DRAWING

FIGURE is a schematic of the process for dehydrogenation of a hydrocarbon using a fast fluidized reactor.

DETAILED DESCRIPTION OF THE INVENTION

The dehydrogenation of hydrocarbons is important for producing olefins. The olefins are important for a variety of products, such as polymer plastics, or the use of olefins in the formation of alkylaryl compounds. A process for the dehydrogenation of propane is presented. The process comprises passing a preheated propane feedstream to a dehydrogenation reactor. The feedstream is contacted with a fluidized catalyst in the dehydrogenation reactor, thereby generating a product stream comprising propylene. The reactor is a fast fluidizing reactor, where the reactor is operated in a flow regime to turbulently mix the catalyst and feedstream. The catalyst and product stream are carried up through the reactor and separated in a separation section, whereby a product stream comprising propylene is passed out of the reactor. A spent catalyst is passed to a catalyst regeneration unit, to regenerate the catalyst for return to the dehydrogenation reactor.

The process of the fast fluidizing reactor is operated at conditions to back-mix the catalyst and reactants. The mixing moderates the temperature to maintain a more uniform temperature during reaction, while limiting local temperature drops that adversely affect the reaction rate. The reaction conditions include operation of the reactor at a temperature between 600° C. and 700° C. The mixing is to provide a more uniform temperature, and it is preferred to sufficiently mix the catalyst and feed to operate at a temperature between 630° C. and 650° C.

The reaction conditions include a pressure at the reactor outlet in the rage from 108 kPa to 170 kPa (1 to 10 psig). The preferred operation controls the pressure at the reactor outlet in the range from 122 kPa to 136 kPa (3 to 5 psig). The reaction operates under an atmosphere comprising hydrogen, in addition to the hydrogen generated. The operation of the reactor includes a hydrogen to hydrocarbon mole ratio at the reactor inlet in the range between 0.2 and 1, with a preferred hydrogen to hydrocarbon mole ratio at approximately 0.6. The feedstream of the hydrogen and hydrocarbon is preheated to provide some of the heat needed for the endothermic reaction. Hydrogen is generated in the dehydrogenation process, and is recovered and recycled to the feedstream. The hydrogen is recycled to maintain a hydrogen level in all regions of the reactor.

The process utilizes relatively short residence times for the catalyst, and also includes rapid regeneration of the catalyst. The process allows for an average catalyst residence time in the reactor of between 15 and 45 minutes, with a preferred average residence time between 15 and 30 minutes. The short cycle time allows for maintaining a more uniform temperature across the reactor to achieve better conversion and selectivity. New catalysts that are useful in this process include non-metal catalysts. The term non-metal catalysts refers to catalysts that do not have metal in its base state, but is meant to refer to catalysts comprising metal oxides, such as zirconia and chromia.

To this extent, the flow of the catalyst during regeneration is limited to an average residence time of less than 30 minutes. The regeneration unit is preferably a riser reactor, which allows for mixing of the catalyst during the regeneration. The regeneration is typically operated under conditions to burn off a portion of the carbon accumulated on the catalyst. Additional fuel is passed to the regeneration unit for combustion and heating of the catalyst. The combustion burns off carbon accumulated on the catalyst during the dehydrogenation process.

The process is shown in the FIGURE. A hydrocarbon feedstream 10 is passed with a hydrogen stream 12 to a combined feed heat exchanger 20, generating a preheated mixed feedstream 22. The mixed feedstream 22 is further heated in a heater 30 to being the heated feedstream 32 to the reactor 40 inlet temperature. The feedstream 32 passed through the reactor 40 and generates a product stream 42 comprising dehydrogenated hydrocarbons. The product stream 42 is used to preheat the hydrogen 12 and hydrocarbon feedstream 10, and produces a partially cooled product stream 24. In the present invention, the preferred feedstock is propane, which is dehydrogenated to form a propylene product stream 42. The catalyst in the reactor flows upward through the reactor 40 and the reactor 40 is operated to provide an average catalyst residence time between 15 and 45 minutes. The catalyst is passed out of the reactor 44 to a regenerator 50. Fuel 46 is added to the regenerator 50 to provide the energy to combust carbon on the catalyst and to heat the catalyst. Air 48 is compressed and heated before being mixed with the fuel 46, and is then passed to the regenerator 50. Additional air and/or fuel 56 can be added to increase the temperature in the regenerator 50. The regenerator 50 is operated to reheat the catalyst, and to pass the catalyst through the regenerator 50 with an averaged residence time of less than 30 minutes. Hot regenerated catalyst 52 is passed to the dehydrogenation reactor 40

The catalyst is circulated at a rapid rate between the reactor 40 and the regenerator 50. The rapid rate of cycling of the catalyst provides heated catalyst on a continuous basis to maintain the endothermic reaction. The rapid cycling generates a low coke amount on the catalyst, and the coke is readily and rapidly removed during the regeneration stage. In addition, excess heat leaving the regenerator in the flue gas 54 can be recovered in steam generation 60. Water 62 is passed to the steam generator to produce steam 64, and a cooled flue gas 66.

It is estimated that the flowscheme will allow for scale up of propylene production to higher flowrates. Current propylene production in a reactor system is limited to around 500 KMTA. The new flowscheme is estimated to increase the production to a flow rate of about 1000 KMTA. For such a system, it is estimated that the catalyst is circulated at a rate in the range of 10 to 12 million kg/hr.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for propane dehydrogenation comprising:
    passing a preheated propane feedstream, comprising hydrogen, to a dehydrogenation reactor, wherein the hydrogen to hydrocarbon mole ratio in the propane feedstream is between 0.2 and 0.6;
    contacting and mixing the propane feedstream with a fluidized catalyst in the dehydrogenation reactor, thereby generating a product stream comprising propylene, wherein the reactor is a fast fluidizing reactor, wherein the catalyst is a non-metal catalyst and wherein the catalyst has an average residence time in the reactor from between 15 and 45 minutes, wherein the catalyst and feedstream are turbulently mixed;
    passing spent catalyst to a catalyst regeneration unit, thereby generating a regenerated catalyst stream; and
    passing the regenerated catalyst stream to the dehydrogenation reactor.

2. The process of claim 1 wherein the fast fluidizing reactor is operated at conditions to back-mix the catalyst and reactants.

3. The process of claim 1 wherein the reaction conditions include a temperature between 600° C. and 700° C.

4. The process of claim 3 wherein the reaction conditions include a temperature between 630° C. and 650° C.

5. The process of claim 1 wherein the reaction conditions include a reactor outlet pressure in the range from 108 kPa to 170 kPa.

6. The process of claim 5 wherein the reaction conditions include a reactor outlet pressure in the range from 122 kPa to 136 kPa.

7. The process of claim 1 wherein the hydrogen to hydrocarbon mole ratio at the feed is approximately 0.6.

8. The process of claim 1 wherein the regeneration unit is a riser reactor, and the catalyst is passed through the regenerator for an average residence time of less than 30 minutes.

9. The process of claim 1 further comprising passing a fuel to the regeneration unit for combustion and heating of the catalyst.

10. The process of claim 1 further comprising passing the product stream to a combined feed heat exchanger to preheat the propane feedstream and to preheat a hydrogen feedstream.

11. The process of claim 1 wherein the catalyst is a metal oxide.

12. The process of claim 1 wherein the catalyst has an average residence time in the reactor from between 15 and 30 minutes.

13. The process of claim 1 wherein the catalyst has an average residence time in the regeneration unit from between 15 and 30 minutes.

14. A process for the dehydrogenation of hydrocarbons comprising:
    combining hydrogen and a paraffin feedstream, thereby forming a combined feedstream, having a hydrogen to hydrocarbon mole ratio in the feedstream of less than 0.6;
    passing the combined feedstream through a combined feed heat exchanger, thereby creating a preheated combined feed;
    heating the preheated combined feed, thereby creating a heated feedstream;
    passing the heated feedstream to a dehydrogenation reactor;
    contacting the heated feedstream with a catalyst, wherein the catalyst is a non-metal catalyst, in the dehydrogenation reactor at conditions such that the reactor is a fast fluidizing reactor, and creating a product stream catalyst mixture, and wherein the catalyst and heated feedstream are turbulently mixed;
    separating the product stream catalyst mixture thereby creating a product stream and a spent catalyst stream;
    passing the product stream to the combined feed heat exchanger to cool the product stream;
    passing the spent catalyst stream to a catalyst regeneration unit, thereby generating a regenerated catalyst stream; and
    passing the regenerated catalyst stream to the dehydrogenation reactor.

15. The process of claim 14 wherein the paraffin feedstream is a propane feedstream.

16. The process of claim 14 wherein the fast fluidizing reactor is operated at conditions to back-mix the catalyst and reactants.

17. The process of claim 14 wherein the catalyst has an average residence time in the reactor from between 15 and 30 minutes.

18. The process of claim 14 wherein the reaction conditions include a temperature between 630° C. and 650° C., a pressure at the reactor outlet between 108 kPa to 170 kPa; and a hydrogen to hydrocarbon mole ratio at the feed is between 0.2 and 0.6.

* * * * *